US00PP33968P2

(12) United States Plant Patent
Lim

(10) Patent No.: US PP33,968 P2
(45) Date of Patent: Feb. 22, 2022

(54) ***AGAPANTHUS* PLANT 'ALTBLOOM'**

(50) Latin Name: ***Agapanthus* hybrid**
Varietal Denomination: ALTBLOOM

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,991

(22) Filed: Jun. 24, 2021

(51) Int. Cl.
*A01H 5/02* (2018.01)
*A01H 6/02* (2018.01)

(52) U.S. Cl.
USPC ..... Plt./398

(58) Field of Classification Search
USPC ..... Plt./263.1, 398
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Agapanthus* plant named 'ALTBLOOM' is disclosed, characterized by a dwarf growth habit, early blooming and large inflorescences resulting in more flowers per plant. The new variety is an *Agapanthus*, typically produced as an ornamental plant.

2 Drawing Sheets

Figure 1:
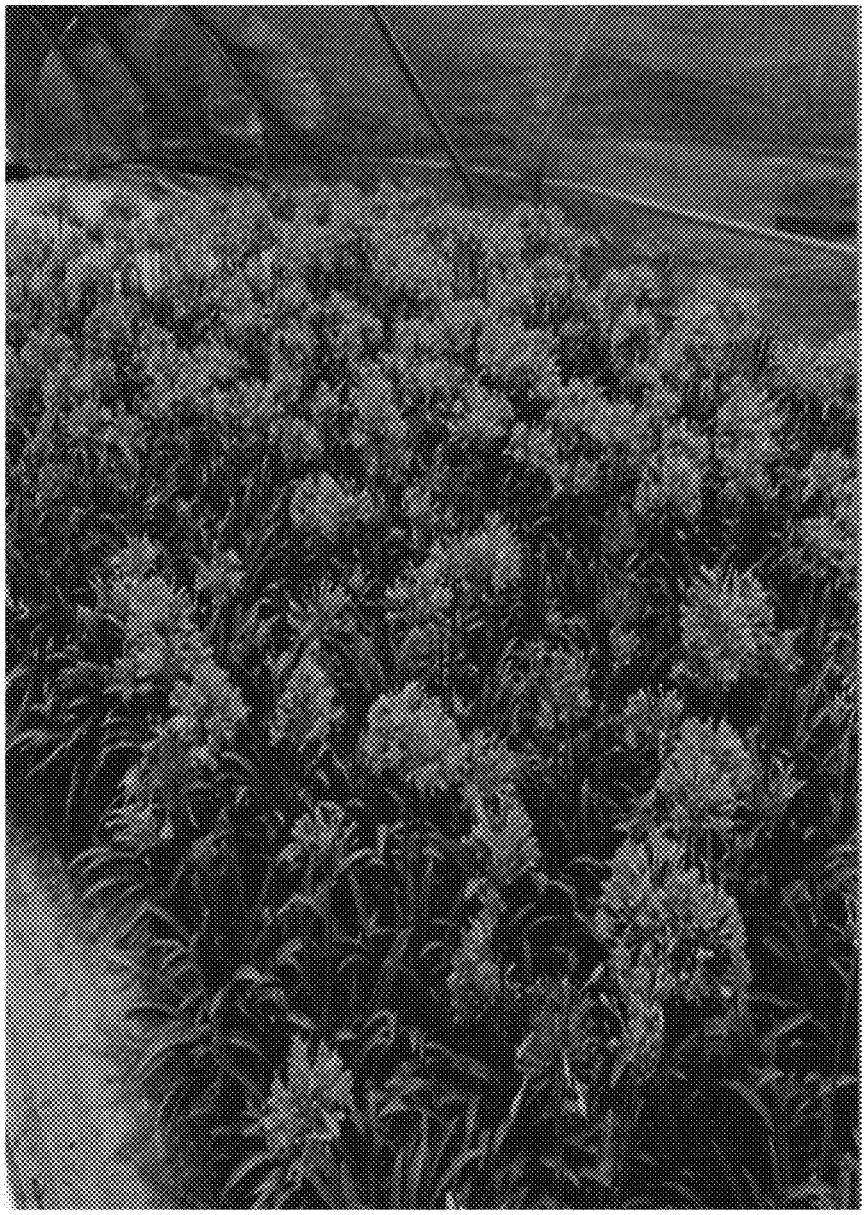

Latin name of the genus and species: *Agapanthus* hybrid.
Variety denomination: 'ALTBLOOM'.

BACKGROUND OF THE INVENTION

The new *Agapanthus* cultivar is the product of a planned breeding program conducted by the inventor, Peter Lim. The open pollination resulting in this new variety was made in July of 2013 at a commercial nursery in Vista, Calif.

The seed parent is the unpatented *Agapanthus* 'Barley Blue'. The pollen parent is an unnamed, unpatented proprietary *Agapanthus*. The new variety was identified and selected as a potentially interesting selection on Jun. 30, 2017, at a commercial nursery in Vista, Calif.

Asexual reproduction of the new cultivar 'ALTBLOOM' was first performed in March of 2017, in Vista, Calif., by tissue culture and division. Subsequent propagation has shown that the unique features of this cultivar are stable and reproduced true to type in successive generations.

SUMMARY OF THE INVENTION

The cultivar 'ALTBLOOM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTBLOOM'. These characteristics in combination distinguish 'ALTBLOOM' as a new and distinct *Agapanthus* cultivar:

1. Dwarf size.
2. Early blooming.
3. Large inflorescences.
4. More flowers per plant than typical of dwarf *Agapanthus*.

5. Light blue flowers.
6. Strong flowering stems.

PARENT COMPARISON

Plants of the new cultivar 'ALTBLOOM' are similar to the seed parent 'Barley Blue', in most horticultural characteristics. However, characteristics of the new cultivar differ in the following:

1. The new variety has a much shorter flowering stem than the seed parent.
2. The new variety blooms earlier than the seed parent.
3. Flowers of the new variety are a darker blue color than the seed parent.
4. Flowers of the new variety have a significant purple vein in the center of the petal, while flowers of the seed parent do not.

COMMERCIAL COMPARISON

Plants of 'ALTBLOOM' are similar in some horticultural characteristics to the variety *Agapanthus* 'Peter Pan', unpatented. The new variety, however, differs in the following:

1. 'ALTBLOOM' blooms earlier than 'Peter Pan'.
2. 'ALTBLOOM' has a shorter stem than 'Peter Pan'.
3. Flowers of 'ALTBLOOM' are a darker blue color than 'Peter Pan'.
4. Flower clusters of 'ALTBLOOM' have more flowers than those of 'Peter Pan'.
5. 'ALTBLOOM' has thicker stems than 'Peter Pan'.

Plants of 'ALTBLOOM' are similar in some horticultural characteristics to the variety *Agapanthus* 'Little Galaxy', application Ser. No. 16/873,015. The new variety, however, differs in the following:

1. 'ALTBLOOM' blooms earlier than 'Little Galaxy'.
2. 'ALTBLOOM' has a larger flower cluster than 'Little Galaxy'.
3. 'ALTBLOOM' has a thicker stem than 'Little Galaxy'.

4. 'ALTBLOOM' has larger leaves than 'Little Galaxy'.
5. 'ALTBLOOM' produces many more flowers than 'Little Galaxy'.

BRIEF DESCRIPTION OF THE PHOTOGRAPHS

The accompanying photograph in FIG. 1 illustrates in full color typical plants of 'ALTBLOOM' grown in a commercial hoop-house in Vista, Calif. The plants are approximately one year old, grown one-gallon pots.

Figure 2:
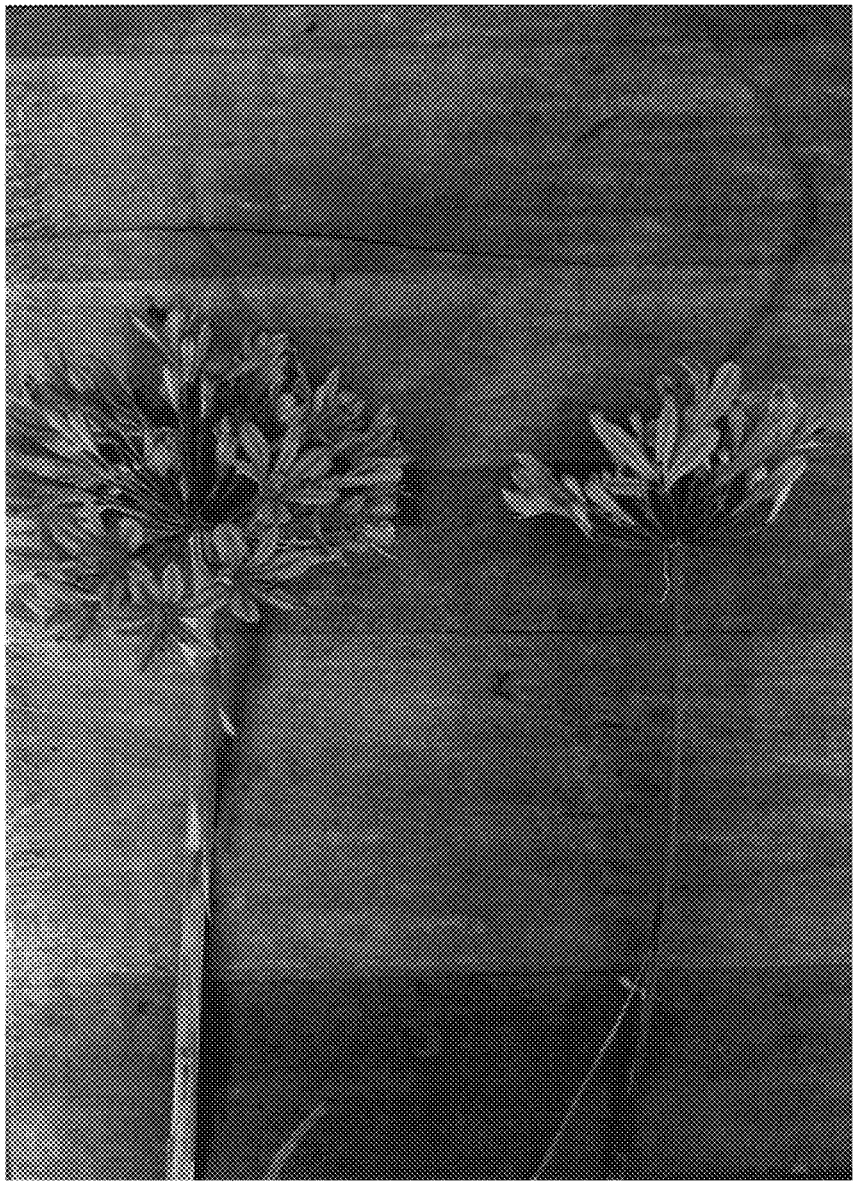

FIG. 2 illustrates a comparison of an inflorescence from the new variety 'ALTBloom' on the left and an inflorescences of the comparator 'Peter Pan' on the right. Inflorescences were harvested from plants grown under the same conditions, at approximately 1 year old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'ALTBLOOM' plant. This plant was grown in a greenhouse in a commercial 1-gallon pot, in Vista, Calif. Plants are approximately 1 year old. Temperatures ranged from 15° C. to 40° C. during the day, and from 10° C. to 25° C. at night. No artificial light, photoperiodic treatments were given to the plants. Measurements and numerical values represent averages of typical plant types.

Botanical classification: *Agapanthus* hybrid 'ALTbloom'.

PROPAGATION

Propagation method: Tissue Culture.

Time to produce a rooted liner: 75 to 100 days at approximately 23° C.

Root description: Long single root with limited branching.

PLANT

Age of plant described: 240 days from a rooted cutting.

Growth habit: Clump forming tender perennial with arching, pendulous foliage. Plants evergreen to about −5° C.

Height: Foliar plane 18 to 22 cm. Flowering plane up to 5 cm.

Plant spread: Approximately 30 to 35 cm.

Growth rate: Moderate.

FOLIAGE

Leaf:

- *Arrangement.*—Basal whorls.
- *Quantity.*—Average 20.
- *Average length.*—16 to 20 cm.
- *Average width.*—1.8 cm.
- *Shape of blade.*—Linear.
- *Apex.*—Acute.
- *Base.*—Truncate, non-clasping.
- *Margin.*—Entire.
- *Aspect.*—Slightly recurved.
- *Venation pattern.*—Linear.
- *Texture of top surface.*—Glabrous.
- *Texture of bottom surface.*—Glabrous.
- *Color.*—Young foliage upper side: Near RHS Green 137C. Young foliage under side: Near RHS Green 137C. Mature foliage upper side: Near RHS Green 137C. Mature foliage under side: Near RHS Green 137C.

FLOWER

Natural flowering season: Begins flowering early June in Southern California.

Length of flowering period: Approximately 8 weeks.

Inflorescence type: Terminal Umbel with approximately 30 individual flowers and 10 buds.

Individual flower type: Single.

Flower profile: Funnelform.

Lasting quality: Inflorescence shows no significant signs of aging for approximately 5 to 6 weeks.

Bud: Measured at approximately 2 to 5 days from opening.

- *Shape.*—Narrow ovate.
- *Length.*—Approximately 3.2 cm.
- *Diameter.*—Approximately 0.7 cm.
- *Color.*—Near RHS Violet-Blue 9A, light, thick streaks near Violet-Blue 90B.

Umbel size:

- *Diameter.*—Average 12 cm.
- *Height.*—Average 7 cm.

Corolla:

- *Arrangement.*—Apetalous, single, campanulate flowers composed of 6 basally fused tepals, shaped into a flared trumpet.
- *Length.*—Approximately 4 cm.
- *Width.*—Approximately 3.5 cm at widest point.
- *Lobe length.*—Approximately 2.6 cm.
- *Lobe width.*—Average 0.7 cm.
- *Margin.*—Entire.
- *Shape.*—Lanceolate.
- *Apex.*—Broadly acute or obtuse.
- *Texture.*—Glabrous all surfaces.

Color:

- *Tepals.*—When opening, upper surface: Near RHS Violet-Blue 97A, strong central streak near 93B. When opening, lower surface: Near RHS Violet-Blue 94D, strong central streak near 93B. Fully opened, upper surface: Near RHS Violet-Blue 94C, strong central streak near 93B. Fully opened, lower surface: Near RHS Violet-Blue 94D, strong central streak near 93C.

Sepals: Not present.

Perianth tube:

- *Length.*—2 cm.
- *Width.*—5 mm.
- *Color.*—Inner surface: Near RHS Violet-Blue 92D. Outer surface: Near RHS Violet-Blue 94C.

REPRODUCTIVE ORGANS

Stamens:

- *Protrusion.*—Weak protrusion past the floral lobe apex.
- *Filament color.*—Upper section near RHS Violet-Blue 92A; lower section near 91D.

Anthers:

- *Quantity.*—6.
- *Length.*—Approximately 3 mm.
- *Color.*—Near RHS Violet-Blue N92B.

Pistil:

*Number.*—1.

*Length.*—Approximately 3.2 cm.

*Style.*—Color: Near RHS Violet-Blue 92B.

*Stigma.*—Shape: Linear. Color: Near RHS Violet-Blue 93B.

Scape:

*Length.*—30 to 35 cm.

*Width.*—7 to 10 mm.

*Texture.*—Glabrous.

*Color.*—Near RHS Green 143C.

Pedicel:

*Length.*—1.6 to 2.5 cm.

*Width.*—2 mm.

*Texture.*—Glabrous.

*Color.*—Near RHS Green 143C.

Fragrance: None.

OTHER CHARACTERISTICS

Seeds: Not observed.

Disease/pest resistance: Neither resistance nor susceptibility to normal diseases and pests of *Agapanthus*.

Temperature tolerance: Not tested but expected to tolerate −5° C. to about 40° C.

Drought tolerance: Will tolerate considerable dryness once established.

What is claimed is:

1. A new and distinct cultivar of *Agapanthus* plant named 'ALTBLOOM' as herein illustrated and described.

* * * * *